United States Patent [19]

Kohn et al.

[11] Patent Number: 5,670,602
[45] Date of Patent: Sep. 23, 1997

[54] SYNTHESIS OF TYROSINE-DERIVED DIPHENOL MONOMERS

[75] Inventors: Joachim B. Kohn; Stephen J. Brocchini, both of Highland Park; Arthur L. Schwartz, East Windsor, all of N.J.

[73] Assignee: Rutgers, The State University, New Brunswick, N.J.

[21] Appl. No.: 625,763

[22] Filed: Mar. 29, 1996

Related U.S. Application Data

[62] Division of Ser. No. 414,339, Mar. 31, 1995, Pat. No. 5,587,507.
[51] Int. Cl.⁶ .................. C08G 63/00; C07C 229/00
[52] U.S. Cl. .................................... 528/176; 560/40
[58] Field of Search ...................... 528/176; 560/40

[56] References Cited

U.S. PATENT DOCUMENTS 5,099,060  3/1992  Kohn et al. ................. 560/40
5,216,115  6/1993  Kohn et al. ................. 528/176

FOREIGN PATENT DOCUMENTS

WO 93/25571  12/1993  WIPO.

OTHER PUBLICATIONS

Bodanszky, Practice of Peptide Synthesis, (Springer–Verlag, New York, 1984) p. 145.

*Primary Examiner*—Joseph Conrad
*Attorney, Agent, or Firm*—Lerner, David, Littenberg, Krumholz & Mentlik

[57] ABSTRACT

A method for preparing diphenol compounds, which method includes the steps of coupling a hydroxyphenyl carboxylic acid with a L-tyrosine ester in a water-miscible organic reaction solvent containing a carbodiimide capable of forming a water-soluble urea by-product, thereby forming a diphenol reaction product; and combining the reaction mixture with an amount of water effective to precipitate the diphenol as a water-immiscible organic phase, so that a water-immiscible organic phase is formed containing the diphenol reaction product. New diphenol monomers and polymers polymerized therefrom are also disclosed.

7 Claims, No Drawings

SYNTHESIS OF TYROSINE-DERIVED DIPHENOL MONOMERS

CROSS-REFERENCE TO RELATED APPLICATIONS

This application is a Divisional of U.S. patent application Ser. No. 08/414,339, filed Mar. 31, 1995, now U.S. Pat. No. 5,587,507 the disclosure of which is incorporated by reference.

GOVERNMENT LICENSE RIGHTS

The U.S. Government has a paid-up license in this invention and the right in limited circumstances to require the patent owner to license others on reasonable terms as required by the terms of Grant No. GM-39455 awarded by the National Institutes of Health.

BACKGROUND OF THE INVENTION

The present invention relates to methods by which L-tyrosine derived diphenol monomers may be synthesized with significantly improved yield and purity. The present invention also relates to new tyrosine-derived diphenol monomers and polymers prepared therefrom.

Diphenols are monomeric starting materials for polycarbonates, polyiminocarbonates, polyarylates, polyurethanes, and the like. Commonly owned U.S. Pat. No. 5,099,060 discloses amino acid-derived diphenol compounds, useful in the polymerization of polycarbonates and polyiminocarbonates. The resulting polymers are useful as degradable polymers in general, and as tissue compatible bioerodible materials for medical uses, in particular. The suitability of these polymers for this end use application is the result of their polymerization from diphenols derived from the naturally occurring amino acid, L-tyrosine. Commonly owned U.S. Pat. No. 5,216,115 discloses polyarylates polymerized from L-tyrosine derived diphenols that are also useful as tissue compatible bioerodible materials for medical uses.

The L-tyrosine derived diphenol monomers are disclosed by the foregoing patents as being prepared by carbodiimide mediated coupling reactions, as disclosed in Bodanszky, *Practice of Peptide Synthesis* (Springer-Verlag, New York, 1984) at page 145. The purification of the L-tyrosine derived diphenols has proved to be difficult. The diphenol crystallizes slowly, precipitating as a water-immiscible oil contaminated with side products of the carbodiimide coupling agent. It has since been discovered that the purity and yield of the diphenol could be improved significantly by the addition of an auxiliary nucleophile such as 1-hydroxybenzotriazole hydrate (HOBt).

Although the purity of the crude diphenol improves significantly, the final purification of the compound remains problematic. A major contaminant is the urea by-product of the carbodiimide. For example, the most commonly available, lowest cost carbodiimide, dicyclohexylcarbodiimide (DCC) has proved highly effective in mediating the formation of L-tyrosine derived diphenol compounds, but produces a by-product, dicyclohexylurea (DCU) that is distributed between the aqueous phase and the water-immiscible diphenol containing phase. The complete removal of DCU by extraction and/or precipitation techniques has not been achieved, which is consistent with previous reports indicating that DCU is difficult to remove from a variety of materials. Consequently, column chromatography is required for the complete purification of L-tyrosine derived diphenol compounds prepared by DCC-mediated coupling reactions.

Column chromatography purification techniques are satisfactory for the small scale preparation of L-tyrosine derived diphenol monomers. However, upon scale-up, several disadvantages become evident, including a reduction in yield, the need to use large amounts of organic solvents as eluents and the inherent difficulties of large scale column chromatography. A method is needed by which L-tyrosine derived diphenol compounds may be prepared without difficult to remove by-products. A method by which such by-products may be readily removed would also be desirable.

WO 93/25,571 describes a method by which peptides containing from 2 to 10 amino acids are synthesized by carbodiimide-mediated amino acid coupling reactions. A solvent in which the urea by-product of the carbodiimide is insoluble is utilized as the reaction solvent, so that the urea by-product precipitates and is removed by filtration. However, the process is not applicable to the synthesis of the L-tyrosine-derived diphenols of this application since the urea by-product remains soluble in the reaction solvent to an appreciable extent. Accordingly, there remains a need for an L-tyrosine coupling method in which carbodiimide by-product formation is prevented or, in the alternative, the removal of such by-products is facilitated.

SUMMARY OF THE INVENTION

This need is met by the present invention. It has now been discovered that the purity and yield of L-tyrosine derived diphenol compounds prepared by carbodiimide mediated coupling reactions can be improved significantly by utilizing a carbodiimide capable of forming a water-soluble urea by-product in a reaction mixture based on a water-miscible organic solvent. Upon completion of the coupling reaction, combining the reaction mixture with water will precipitate the diphenol product as a water-immiscible organic phase with most of the urea by-product of the carbodiimide remaining in the water-miscible reaction mixture. Any urea by-product remaining in the diphenol phase may be removed by backwashing the organic phase with an aqueous extraction medium.

Therefore, according to one aspect of the present invention, an improved carbodiimide-mediated coupling reaction is provided for the preparation of L-tyrosine derived diphenol compounds. According to this aspect of the invention, a method is provided for preparing diphenol compounds having the structure of Formula I:

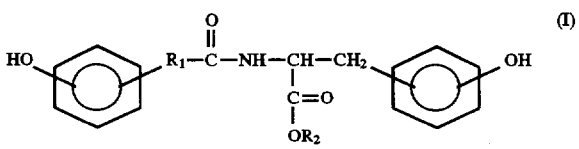

wherein $R_1$ is —CH=CH— or (—CH$_2$—)$_n$, in which n is zero or an integer from one to eight; and $R_2$ is selected from straight and branched alkyl and alkylaryl groups containing up to 18 carbon atoms; which method includes the step of:

coupling a hydroxyphenyl carboxylic acid having the structure of Formula II:

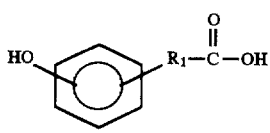

with a tyrosine ester having the structure of formula III:

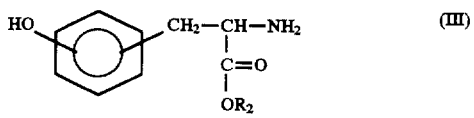

in a water-miscible organic reaction solvent containing a carbodiimide capable of forming a water-soluble urea by-product thereby forming a diphenol reaction product. Upon completion of the coupling reaction, the reaction mixture is combined with an amount of water effective to precipitate the diphenol as a water-immiscible organic phase. In this way, two phases are formed, a water-immiscible organic phase containing the bulk of the diphenol reaction product, and an aqueous phase containing the bulk of the water-soluble urea and unreacted starting materials.

In preferred methods in accordance with the present invention, the separated water-immiscible organic phase is washed with an aqueous extraction medium and then separated from the extraction medium. Regardless of whether the washing step is performed, preferred methods in accordance with the present invention precipitate the diphenol reaction product in the form of a water-immiscible phase.

Attendant with the discovery of the improved synthesis method of the present invention, it was also learned that other hydroxyphenyl carboxylic acids could be coupled with L-tyrosine to produce diphenol compounds useful as monomers in the polymerization of tissue compatible bioerodible polymers for biomedical uses. Such hydroxyphenyl carboxylic acids include hydroxycinnamic acid and certain hydroxyphenylalkyl carboxylic acids. The monomers provided by this aspect of the present invention are diphenol compounds having the structure of Formula I wherein $R_1$ is —CH=CH—, or (—CH$_2$—)$_n$, in which n is zero, one, or an integer from three to eight, and $R_2$ is selected from straight and branched alkyl and alkylaryl groups containing up to 18 carbon atoms.

The present invention also includes polycarbonates prepared from the monomers of the present invention by the process disclosed by U.S. Pat. No. 5,198,507 and polyarylates prepared from the monomers of the present invention by the process disclosed by U.S. Pat. No. 5,216,115.

The present invention provides L-tyrosine derived diphenol monomers at significantly reduced cost with sufficient purity for polymerization to high molecular weight tissue compatible bioerodible polymers for biomedical uses.

DETAILED DESCRIPTION OF THE PREFERRED EMBODIMENTS

The method of the present invention prepares diphenol compounds derived from L-tyrosine as a starting material. L-tyrosine is a naturally-occurring amino acid. The diphenols prepared by the method of the present invention have the structure of Formula I in which $R_1$ and $R_2$ are the same as described above with respect to Formula I. Among the preferred L-tyrosine derivatives of Formula I are derivatives in which $R_1$ is —CH$_2$—CH$_2$—. These preferred compounds are tyrosine dipeptide analogues known as desaminotyrosyl-tyrosine alkyl esters. Desaminotyrosine (Dat) itself occurs naturally in plants. In this preferred group, the diphenol can be regarded as a derivative of tyrosyl-tyrosine dipeptide from which the N-terminal amino group has been removed.

The desaminotyrosyl-tyrosine compounds prepared by the method of the present invention are more properly referred to as desaminotyrosyl-tyrosine alkyl or alkylaryl esters. The preferred monomers of the group of desaminotyrosyl-tyrosine alkyl esters are the ethyl, butyl, hexyl, octyl and benzyl esters. The most preferred ester is the ethyl ester, referred to as desaminotyrosyl-tyrosine ethyl ester, or DTE. New insights lead us to believe that DTE may be more suitable than desaminotyrosyl-tyrosine hexyl ester, or DTH, for most cell-polymer interactions. However, in all previous patents, DTH was regarded as most preferred.

The method of the present invention prepares the diphenol compounds of Formula I by reacting the hydroxyphenyl carboxylic acid of Formula II, in which $R_1$ is the same as described above with respect to Formula I, with a C-terminus protected tyrosine. C-terminus protected tyrosine suitable for use with the present invention are depicted in Formula III, in which $R_2$ is the same as described above with respect to Formula I. Such C-terminus protection is obtained by the formation of alkyl and alkylaryl esters of the C-terminus. C-terminus protecting alkyl and alkylaryl esters of tyrosine containing up to eight carbon atoms are prepared according to the procedure disclosed in J. P. Greenstein and M. Winitz, *Chemistry of the Amino Acids* (John Wiley & Sons, New York 1961), p.927–929. C-terminus protecting alkyl and alkylaryl esters of tyrosine containing more than eight carbon atoms are prepared according to the procedure disclosed in Overell, U.S. Pat. No. 4,428,932.

If the tyrosine alkyl or alkylaryl esters are initially obtained in their salt-form, the salts are removed by a simple treatment with aqueous base. The diphenol compounds are then prepared by coupling reactions mediated by carbodiimides capable of forming water-soluble urea by-products in a water-miscible organic reaction solvent in which the carbodiimide, the hydroxyphenyl carboxylic acid and the tyrosine ester are soluble. Examples of carbodiimides suitable for use with the present invention that form water-soluble urea by-products include 1-ethyl-3-(3-dimethylaminopropyl)carbodiimide hydrochloride (EDCI.HCl), 1-alkyl-3-(3-dimethylaminopropyl) carbodiimide (alkyl=isopropyl, cyclohexyl), 1-cyclohexyl-3-(2-morpholinyl-(4)-ethyl)carbodiimide, 1-cyclohexyl-3-(4-diethylaminoohexyl)carbodiimide, 1-cyclohexyl-3-(β-diethylaminoethyl)carbodiimide, 1,3-di-(4-diethylaminocyclohexyl)carbodiimide, 1-alkyl-3-(3-morpholinyl-(4)-propyl)carbodiimide (alkyl=methyl, ethyl), 1-benzyl-3-(3-dimethylamino-(N)-propyl)carbodiimide, 1-ethyl-3-(4-azonia-4,4-di-methylpentyl)carbodiimide; in each case—as the free base or salt (HCl; methiodide; metho p-toluenesulfonate). The preferred carbodiimide is EDCI-.HCl.

Examples of suitable water-miscible organic solvents include tetrahydrofuran (THF), dioxane, dimethoxyethane, acetone, N-methyl pyrrolidinone, acetonitrile. The preferred solvent is THF.

The method of the invention otherwise essentially follows standard procedures of peptide chemistry such as are disclosed in the above-cited *Practice of Peptide Synthesis*. Typically, equimolar quantifies of the hydroxylphenyl carboxylic acid and tyrosine ester are placed in a reaction vessel equipped with stirring means. The vessel is sealed and blanketed with an inert gas such as nitrogen, and a sufficient quantity of solvent is added to dissolve the hydroxyphenyl carboxylic acid and tyrosine ester, as well as the carbodiimide to be added. This quantity of solvent can be readily determined by one of ordinary skill in the art without undue experimentation.

The reaction mixture is then cooled to a temperature of about 0° C. prior to addition of the carbodiimide, which is then added to the reaction mixture while maintaining the inert blanket. The reaction mixture is then stirred at the reduced temperature for at least one hour and allowed to gradually return to room temperature with stirring for at least 1 hour, and preferably 19 hours.

The reaction mixture is then combined with an amount of water effective to precipitate the diphenol reaction product as a water-immiscible organic phase. At least 2 volumes of water are utilized relative to the reaction solvent, and preferably about 10 volumes of water.

Alternatively, the reaction solvent may be evaporated to leave a concentrated syrup-like residue. The residue is then washed with water to precipitate the diphenol reaction product as a water-immiscible organic phase, while the urea by-product is extracted into the aqueous phase.

The diphenol-containing water-immiscible organic phase is then separated from the aqueous phase, typically by addition of a water-immiscible organic solvent such as methylene chloride, chloroform, or ethyl acetate. The purpose of adding the water-immiscible solvent at this stage is to dilute the highly concentrated diphenol-containing residue and to facilitate the separation of the diphenol from the aqueous phase. The preferred solvent for preparation of DTE is ethyl acetate, and for preparation of all other monomers is methylene chloride. At least 2 volumes of the extraction solvent should be utilized relative to the original quantity of reaction solvent employed.

At this stage, the organic phase may be dried over $MgSO_4$ or $Na_2SO_4$, filtered and concentrated to an oil that may be placed under hexane to precipitate highly pure crystals of the diphenol reaction product. Preferably, the water-immiscible organic phase is backwashed with either or both aqueous acid and mild base extraction media to further purify the organic phase of water-soluble contaminants. Preferably, the organic phase is ultimately washed with multiple portions of both acid and mild base aqueous extraction media. For example, the organic phase may first be washed with multiple portions of 0.1M $Na_2CO_3$, followed by multiple portions of saturated NaCl, multiple portions of 0.1M citric acid or hydrochloric acid and multiple portions of saturated NaCl. The volume of extraction media to be utilized for each portion is well known by those of ordinary skill in the art and should be slightly greater in volume than the organic phase.

The aqueous layers are preferably further backwashed with equal volumes of the organic phase solvent. The organic phases should then be combined, dried over $MgSO_4$, filtered and concentrated to an oil, from which the diphenol reaction product may be recovered under hexane as described above.

In addition to the diphenol compounds described by U.S. Pat. No. 5,216,115, the method of the present invention may be utilized to prepare the diphenol compounds of Formula I wherein $R_1$ is —CH=CH— or (—$CH_2$—)$_n$, in which n is zero or one, or an integer from three to eight, and $R_2$ is selected from straight and branched alkyl and alkylaryl groups containing up to 18 carbon atoms. $R_1$ is preferably (—$CH_2$—)n, wherein n is two. $R_2$ is preferably ethyl, butyl, hexyl octyl or benzyl. Most preferably, $R_2$ is ethyl. These diphenol compounds may also be prepared utilizing the methods described by the aforementioned U.S. Pat. No. 5,216,115, the disclosure of which is hereby incorporated herein by reference.

The diphenol compounds are then polymerized to form tissue compatible bioerodible polymers for medical uses. For example, the diphenol compounds may be polymerized to form polyiminocarbonates via one of the appropriate methods disclosed by U.S. Pat. No. 4,980,449, the disclosure of which is hereby incorporated herein by reference thereto. According to one method, part of the diphenol is converted to the appropriate dicyanate, then, equimolar quantifies of the diphenol and the dicyanate are polymerized in the presence of a strong base catalyst such as a metal alkoxide or metal hydroxide. The resulting polyiminocarbonate will have the structure of Formula IV:

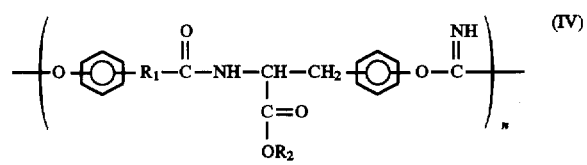

in which $R_1$ and $R_2$ are the same as described above with respect to Formula I.

U.S. Pat. No. 4,980,449 also describes an interfacial polymerization method by which the polyiminocarbonate of Formula IV may be synthesized. In this method, an aqueous phase containing the diphenol and the strong base catalyst is contacted with an organic phase containing the dicyanate dissolved in a water immiscible solvent. A phase transfer catalyst is first added to the dicyanate solution, which is then contacted with the aqueous diphenol solution with vigorous mixing. Upon thorough mixing of the two phases, a polyiminocarbonate precipitate forms.

According to yet another method disclosed by U.S. Pat. No. 4,980,449, the diphenol may be reacted with cyanogen bromide in an interfacial polymerization to form a polyiminocarbonate having essentially the structure shown in Formula IV in which $R_1$ and $R_2$ are the same as described above with respect to Formula I.

The diphenol compounds may also be reacted with phosgene to form polycarbonates by the method described by U.S. Pat. No. 5,099,060, the disclosure of which is hereby incorporated by reference thereto. The described method is essentially the conventional method for polymerizing diphenols into polycarbonates. Suitable processes, associated catalysts and solvents are known in the art and are taught in Schnell, *Chemistry and Physics of Polycarbonates*, (Interscience, New York 1964), the teachings of which are also incorporated herein by reference. Polycarbonates prepared in accordance with these methods utilizing the diphenols of the present invention have repeating structural units with the structure of Formula V:

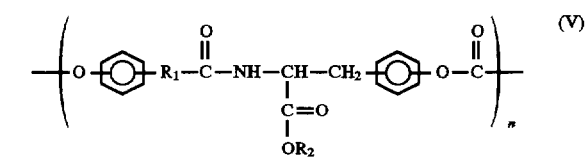

in which $R_1$ and $R_2$ are the same as described above with respect to Formula I.

The diphenol compounds may also be reacted according to the method disclosed by U.S. Pat. No. 5,216,115 to form polyarylates, the disclosure of which is hereby incorporated by reference thereto.

As disclosed by U.S. Pat. No. 5,216,115, the diphenol compounds are reacted with aliphatic or aromatic dicarboxylic acids in a carbodiimide mediated direct polyesterification using 4-(dimethyl-amino)pyridinium-p-toluene sulfonate (DPTS) as a catalyst to form aliphatic or aromatic polyarylates. Dicarboxylic acids suitable for the polymerization of polyarylates have the structure of Formula VI or VII:

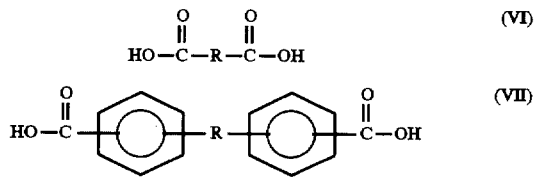

in which, for the aliphatic polyarylates, R is selected from saturated and unsaturated, substituted and unsubstituted alkyl or alkylaryl groups containing up to 18 carbon atoms, and preferably from 2 to 12 carbon atoms. For the aromatic polyarylates, R is selected from aryl groups containing up to 18 carbon atoms and preferably from 6 to 12 carbon atoms. The resulting aliphatic polyarylate has the structure of Formula VIII; while the resulting aromatic polyarylate has the structure of Formula IX:

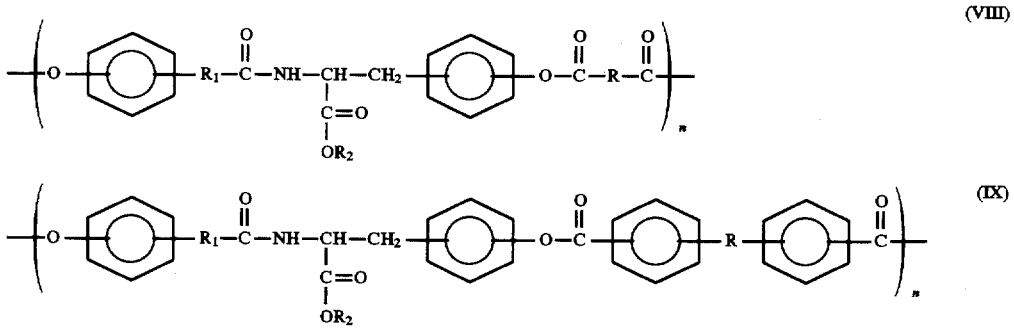

in which R is the same as described above with respect to Formula VI and $R_1$ and $R_2$ are the same as described above with respect to Formula I.

The diphenols of the present invention provide polyiminocarbonates having weight average molecular weights above about 60,000 daltons, up to about 200,000 daltons, and higher, calculated from gel permeation chromatography (GPC) relative to polystyrene standards without further correction. The diphenols of the present invention form polycarbonates having weight-average molecular weights above about 50,000 daltons, and preferably above 100,000 daltons, calculated from GPC relative to polystyrene standards without further correction. The diphenol compounds of the present invention provide polyarylates having weight average molecular weights above about 50,000 daltons, and preferably above 100,000 daltons, calculated from GPC relative to polystyrene standards without further correction.

The polymers can be worked up by known methods commonly employed in the field of synthetic polymers to produce a variety of useful articles with valuable physical and chemical properties, all derived from tissue compatible monomers. The useful articles can be shaped by conventional polymer-forming techniques such as extrusion, compression molding, injection molding, solvent casting, wet spinning, and the like. Shaped articles prepared from the polymers are useful, inter alia, as degradable biomaterials for medical implant applications. Such applications include the use of the shaped articles as vascular grafts and stents, bone plates, sutures, implantable sensors, barriers for surgical adhesion prevention, implantable drug delivery devices, scaffolds for tissue regeneration, and other therapeutic aids and articles which decompose harmlessly within a known period of time.

The polyiminocarbonates degrade rapidly to low-molecular weight species, while their polycarbonate counterparts degrade very slowly. The polyarylate counterparts have a moderate rate of hydrolytic degradation. The polyiminocarbonates and polycarbonates may also be blended to provide a material having an intermediate rate of biodegradation.

The following non-limiting examples set forth hereinbelow illustrate certain aspects of the invention. All parts and percentages are by weight unless otherwise noted and all temperatures are in degrees Celsius. L-tyrosine, Dat, hexanol, octanol, butanol, HOBt and DCC were purchased from Aldrich (Milwaukee, Wis.). Hexane was purchased from Fisher (Springfield, N.J.). Fluka (Ronkonkoma, N.Y.) was the supplier of phosgene. EDCLHCl was from JBL Scientific (San Luis Obispo, Calif.). All solvents were HPLC Fade. THF was distilled from sodium and benzophenone. All other reagents were of analytical grade and were used as received.

EXAMPLES

The examples use the following product characterization procedures.

SPECTROSCOPY $^1$H NMR spectra were recorded at 199.98 MHz on a Varian Gemini 200 in 5 mm tubes at 10% (w/v) in deuterated solvents. Chemical shifts were reported in ppm.

MOLECULAR WEIGHTS

Molecular weights were determined by GPC on a chromatographic system consisting of a Perkin-Elmer Model 410 pump, a Waters Model 410 Refractive Index Detector, and a Perkin-Elmer Model 2600 computerized data station. Two PL-gel GPC columns ($10^5$ and $10^3$ Angstrom pore size, 30 cm length) were operated in series at a flow rate of 1 mL/min in THF. Polymer solutions (5 mg/mL) were prepared, filtered (0.45 micron membrane filter) and allowed to equilibrate for 30 min prior to injection. The injection volume was 25 microliters. Molecular weights were calculated relative to polystyrene standards (Polymer Laboratories, Inc.) without further corrections.

THERMAL ANALYSIS

Determination of product purity was based on melting point depression measured with a TA Instruments 910 Differential Scanning Calorimeter (DSC) calibrated with indium. For determination of the melting temperature, a 2.0 mg sample was subjected to a single run at a heating rate of 1° C./min over a 60° C. range.

THIN LAYER CHROMATOGRAPHY (TLC)

TLC was run on 250 micron silica gel, aluminum-backed plates with fluorescent indicator. Plates were eluted with 100:10 methylene chloride:methanol and compounds were visualized with phosphomolybdic acid.

The following Table defines the abbreviations adopted for the diphenols illustrated by the examples below:

TABLE I

| | |
|---|---|
| Desaminotyrosyl tyrosine ethyl ester | DTE |
| Desaminotyrosyl tyrosine butyl ester | DTB |
| Desaminotyrosyl tyrosine hexyl ester | DTH |
| Desaminotyrosyl tyrosine octyl ester | DTO |

Ethyl, butyl, hexyl and octyl esters of tyrosine were synthesized using the protocol of Ertel et at., *J. Biomed. Mater. Res.*, 28, 919 (1994).

Example 1

Preparation of DTH

Tyrosine hexyl ester (9.63 g, 36.3 mmol) and Dat (6.04 g, 36.3 mmol) were placed in a three-necked round bottom flask with a magnetic stir bar. The flask was sealed and flushed with nitrogen. 60 mL of freshly distilled THF was added by syringe. The reaction mixture was chilled in an ice bath for 10 minutes. Then EDCI.HCl (7.67 g, 40.0 mmol) was added while the nitrogen blanket was maintained. The reaction mixture stirred for one hour in an ice bath and for 19 hours at room temperature.

The reaction mixture was poured with stirring into 600 mL of water. An oil formed, which was removed by extraction into 120 mL of methylene chloride. The organic layer was washed with two portions of 200 mL of 0.1M $Na_2CO_3$, two portions of 200 mL of saturated NaCl, two portions of 200 mL of 0.1M of citric acid, and two portions of 200 mL of saturated NaCl. All aqueous layers were backwashed with 10 mL of methylene chloride. The organic phases were combined, dried over $MgSO_4$, filtered and concentrated to an oil. The yellow oil was placed under hexane to yield almost colorless crystal. Product yield and purity are listed in Table II. $^1$H-NMR ($CDCl_3$):0.86 (t, 3H), 1.30 (s, 6H), 1.63 (m, 2H), 2.46 (m, 2H), 2.90 (m, 4H), 4.10 (t, 2H), 4.80 (q, 1H), 6.00 (d, 1H), 6.70 (m, 6H), 6.95 (d, 2H).

Example 2

Preparation of DTE

The procedure of Example 1 was repeated, substituting tyrosine ethyl ester (4.00 g, 19.0 mmol) for the tyrosine hexyl ester. Ethyl acetate was substituted for methylene chloride as the extraction solvent. Product yield and purity are listed in Table II. Elemental analysis: calculated: 67.0% C, 6.8% H, 3.9% N; experimental: 66.9% C, 6.6% H, 3.7% N. $^1$H-NMR ($CDCl_3$): 1.24 (t, 3H), 2.45 (m, 2H), 2.95 (m, 4H), 4.20 (q, 2H), 4.83 (q, 1H), 5.90 (d, 1H), 6.70 (m, 6H), 7.00 (d, 2H).

Example 3

Preparation of DTB

The procedure of Example 1 was repeated, substituting tyrosine butyl ester (7.50 g, 31.6 mmol) for the tyrosine hexyl ester. Product yield and purity are listed in Table II. Elemental analysis: calculated: 68.4% C, 7.3% H, 3.6% N; experimental: 68.5% C, 7.2% H, 3.4% N. $^1$H-NMR ($CDCl_3$): 0.930 (t, 3H), 1.30 (m, 2H), 1.64 (m, 2H), 2.46 (m, 2H), 2.90 (m, 4H), 4.10 (t, 2H), 4.80 (q, 1H), 5.90 (d, 1H), 6.70 (m, 6H), 6.95 (d, 2H).

Example 4

Preparation of DTO

The procedure of Example 1 was repeated, substituting tyrosine octyl ester (2.00 g, 6.81 mmol) for the tyrosine hexyl ester. Product yield and purity are listed in Table II. Elemental analysis: calculated: 70.6% C, 8.2% H, 3.2% N; experimental: 70.0% C, 8.0% H, 3.0% N. $^1$H-NMR ($CDCl_3$): 0.88 (t, 3H), 1.28 (s, 10H), 1.60 (m, 2H), 2.40 (m, 2H), 2.90 (m, 4H), 4.10 (t, 2H), 4.80 (q, 1H), 5.90 (d, 1H), 6.70 (m, 6H), 7.00 (d, 2H).

COMPARATIVE EXAMPLE

DTB, DTE, DTH and DTO were prepared in coupling reactions using DCC/HOBt as the coupling agent, following the protocol of Ertel et al. Product yield, purity and melting point compared to the diphenols of Examples 1–4 are shown in Table II.

TABLE II

| | COUPLING AGENTS | | | |
|---|---|---|---|---|
| | Coupling With DCC/HOBt | | Coupling With EDCI.HCl | |
| Product | Yield[a] (%) | Purity[b] (%) | Yield[a] (%) | Purity[b] (%) |
| DTE | 65 | 97.9 | 71 | 95.8 |
| DTB | 71 | 98.3 | 76 | 96.3 |
| DTH | 54 | 98.2 | 68 | 98.9 |
| DTO | 64 | 98.1 | 40 | 97.7 |

[a] pure DTH, calculation based on amount of Dat present in the coupling step
[b] purity evaluated by melting point depression measure by DSC The purity and yield of the diphenols prepared by using EDCI.HCl as the coupling agent were comparable to the values obtained for diphenols prepared using DCC/HOBt as the coupling agent. TLC analysis of the diphenols prepared by EDCI.HCl revealed the presence of several trace impurities of higher $R_f$ value than desaminotyrosyl-tyrosine alkyl esters prepared by DCC/HOBt. To explore the effect of these contaminants on the polymerization reaction, the monomers of Examples 1–4 were polymerized with phosgene.

EXAMPLES 5–8

The diphenols of Examples 1–4 were polymerized in solution with phosgene as described by Pulapura et at., *Biopolymers*, 32, 411 (1992). The polymers were purified by precipitation of a 10% (w/v) polymer solution in methylene chloride into twice the volume of methanol. Weight-average and number-average molecular weights for representative batches of the polymers are shown in Table III.

TABLE III

| | Monomer Prepared by EDCI.HCl | |
|---|---|---|
| Polymer | Mw | Mn |
| poly(DTE carbonate) | 161,000[c] | 70,000[c] |
| | 104,000[c] | 47,000[c] |
| poly(DTB carbonate) | 117,000[c] | 56,000[c] |
| poly(DTH carbonate) | 195,000[c] | 88,000[c] |
| | 200,000[c] | 85,000[c] |
| poly(DTO carbonate) | 240,000[c] | 108,000[c] |

[c] measured by GPC in THF, relative to polystyrene standards

Because the polymerization reaction proceeds through a condensation at the phenolic hydroxyl groups, the presence of any monofunctional compounds would lead to the premature termination of chain growth and result in the formation of polymers of low molecular weight. However, Table III illustrates that monomers prepared using EDCI.HCl as the coupling agent provide high molecular weight polymers. Initial evaluations indicate that monomers prepared with EDCI.HCl coupling agents give rise to polymers with identical physicomechanical properties to polymers of monomers prepared using DCC/HOBt as the coupling agent.

The use of EDCI.HCl in the coupling reaction has several significant advantages over the use of DCC/HOBt. First of all, EDCI.HCl yielded a relatively pure product in the absence of an auxiliary nucleophile such as HOBt. This is significant because many investigators select DCC over other carbodiimide coupling agents because of its lower price. However, on a molar basis, the combination of DCC/HOBt is comparable in cost to EDCI.HCl. Second, the use of EDCI.HCl in place of DCC made it possible to replace column chromatography in organic solvents by simple precipitations/extractions in aqueous media as the main technique of product purification. In view of environmental concerns relating to the large-scale use of organic solvents, this is a significant advantage.

In summary, in large-scale synthesis, when convenience and cost become critical factors, the method of the present invention, utilizing carbodiimides capable of forming water-soluble urea by-products, provides an advantageous means by which L-tyrosine-derived diphenol monomers may be synthesized. The method of the present invention yields the diphenol monomers at significantly reduced cost in an environmentally-acceptable procedure with sufficient purity for polymerization to high molecular weight polymers.

The foregoing examples and description of the preferred embodiment should be taken as illustrating, rather than as limiting, the present invention as defined by the claims. As will be readily appreciated, numerous variations and combinations of the features set forth above can be utilized without departing from the present invention as set forth in the claims. Such variations are not regarded as a departure from the spirit and scope of the invention, and all such modifications are intended to be included within the scope of the following claims.

What is claimed is:

1. An L-tyrosine derived diphenol compound having the structure:

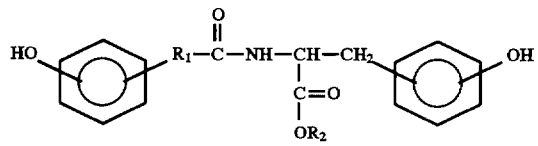

wherein $R_1$ is selected from the group consisting of $-CH=CH-$, $-CH_2-$, and $(-CH_2-)_n$, in which n is zero, one, or an integer from three to eight; and $R_2$ is selected from the group consisting of straight and branched and alkyl alkylaryl groups containing up to 18 carbon atoms.

2. The diphenol of claim 1, wherein $R_1$ is $-CH_2-$.

3. The diphenol of claim 1, wherein $R_1$ is $(-CH_2-)_n$, in which n is zero or three.

4. The diphenol compound of claim 1, wherein $R_2$ is selected from the group consisting of ethyl, butyl, hexyl, octyl and benzyl groups.

5. The diphenyl compound of claim 4, wherein $R_2$ is a ethyl group.

6. A polycarbonate polymerized from the diphenol compound of claim 1.

7. A polyarylate polymerized from the diphenol compound of claim 1.

* * * * *

UNITED STATES PATENT AND TRADEMARK OFFICE
CERTIFICATE OF CORRECTION

PATENT NO. : 5,670,602
DATED : September 23, 1997
INVENTOR(S) : Kohn et al.

It is certified that error appears in the above-identified patent and that said Letters Patent is hereby corrected as shown below:

Delete "EDCI.HCl" throughout the patent and substitute --EDCI•HCl-- therefor.

Column 4, line 47 "diethylaminoohexyl" should read --diethylaminocyclohexyl--.

Column 5, line 64, "(-CH$_2$-)n" should read -- (-CH$_2$-)$_n$--.

Column 5, line 65, "hexyl octyl" should read --hexyl, octyl--.

Column 8, line 20, "Fade" should read --grade--.

Column 12, line 21 (within claim 1), "branched and alkyl" should read --branched alkyl and--.

Signed and Sealed this

Twentieth Day of January, 1998

Attest:

BRUCE LEHMAN

*Attesting Officer*  *Commissioner of Patents and Trademarks*